(12) United States Patent
Kulkarni et al.

(10) Patent No.: US 6,495,695 B2
(45) Date of Patent: Dec. 17, 2002

(54) PROCESS FOR THE PREPARATION OF A COLLIDINE AND 2,3,5,6-TETRAMETHYL PYRIDINE

(75) Inventors: Shivanand Janardan Kulkarni, Andhra Pradesh (IN); Kondapuram Vijaya Raghavan, Andhra Pradesh (IN); Srinivas Nagabandi, Andhra Pradesh (IN); Radha Rani Vippagunta, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/818,279

(22) Filed: Mar. 27, 2001

(65) Prior Publication Data

US 2002/0173660 A1 Nov. 21, 2002

(51) Int. Cl.$^7$ ............................................. C07D 213/02
(52) U.S. Cl. ...................................................... 546/348
(58) Field of Search ......................................... 546/348

(56) References Cited

FOREIGN PATENT DOCUMENTS

EP         885884 A1  *  12/1998

OTHER PUBLICATIONS

Stamm et al, Journal of Catalysis, vol. 155, No. 2, pp. 268–282, Mar. 1995.*

* cited by examiner

*Primary Examiner*—Zinna Northington Davis
(74) *Attorney, Agent, or Firm*—Ladas & Parry

(57) ABSTRACT

The present invention provides a process for synthesis of tri- and tetra-alkylated pyridines (i.e. collidines) in high yields by reacting methyl ethyl ketone with formaldehyde in presence of ammonia in gas phase in the presence of a zeolite catalyst which comprises of silica-alumina with at least one metal ion and/or metal selected from the group consisting of lanthanum, lead, manganese, iron, copper and cobalt. This process provides eco-friendly, more economical and shape-selective heterogeneous method.

16 Claims, No Drawings

PROCESS FOR THE PREPARATION OF A COLLIDINE AND 2,3,5,6-TETRAMETHYL PYRIDINE

FIELD OF THE INVENTION

The present invention relates to a process for the preparation of a collidine and 2,3,5,6-tetramethyl pyridine over a zeolite catalyst. More particularly, the present invention relates to a process for the preparation of collidine from methyl ethyl ketone, formaldehyde and ammonia in gas phase in an eco-friendly method with high yields and selectivity.

The present invention provides a non-corrosive, eco-friendly process where the catalyst can be recycled and reused for many times. The process involves no-wastage of the compounds (i.e. high atom selectivity) and has high selectivity of products.

BACKGROUND OF THE INVENTION

Collidines and tetramethyl pyridines are useful compounds that find application as raw materials in various medicines like Omeprazole and also in agrochemicals.

The following processes are known for the preparation of 2,3,5-collidine by reacting a carbonyl compound with ammonia in a gas phase in the presence of a catalyst.

A process comprising reacting methacrolein and methyl ethyl ketone with ammonia in a gas phase in presence of catalyst which comprises silica-alumina containing at least one element selected from the group consisting of cobalt, zinc, cadmium and lead. (U.S. Pat. No. 6,111,113) wherein the yield of 2,3,5-collidine is 42% and other major product is 2-methyl 5-ethyl pyridine.

A process comprising reacting methacrolein with ammonia in a gas phase in the presence of a catalyst which comprises silicon and an element such as zirconium, aluminium and/or phosphorus (see JP-A-8-245589), and a process comprising reacting methacrolein and methyl ethyl ketone with ammonia in a gas phase in the presence of an oxide catalyst comprising silicon, phosphorus and/or boron (see JP-A-8-259537). However, the main product of the former process is 3,5-lutidine, while 2,3,5-collidine is obtained in a yield of only 16.5%. In the latter process, 2,3,5-collidine is obtained in a yield of 15 to 37%.

Another process by Yamaji; Mitsuharu comprises the synthesis of collidine along with tetramethyl pyridine by the alkylation of 3,5-lutidine with aliphatic alcohols over Raney nickel catalysts. The yields and selectivities are higher but the process suffers from use of hydrogen and is not a continuous process.

Some processes have also been reported such as the separation of 2,3,5-collidine from tar and the reacting the 3,5-lutidine methyl lithium butyl but these or not upto the level of commercial use. In the latter process the yield is upto 80% but suffers in industrial operation.

Syntheses of pyridine bases have been extensively studied over the solid acid catalysts and on some zeolites, but those are not for the synthesis of collidines and tetramethyl pyridines. Prior art describes neither a gas phase catalytic reaction of a carbonyl compound with formaldehyde and ammonia for the preparation of collidines, nor the use of crystalline uniform porous zeolite catalysts.

OBJECTS OF THE INVENTION

The main object of the present invention is to provide a process for the synthesis of collidines over zeolite molecular sieves in a heterogeneous eco-friendly method.

Another object of the present invention is to provide a process for the preparation of collidines, in a high yield and at the same time, 2,3,5,6-tetramethyl pyridine, by the gas phase catalytic reaction of a carbonyl compound and ammonia.

Another object of the present invention is to provide a process for synthesizing collidines using a specific zeolite catalyst.

Another object of the invention is to provide a process wherein the catalyst is capable of reuse and recycling.

SUMMARY OF THE INVENTION

Accordingly the present invention relates to a process for the preparation of a compound of formula 1

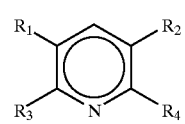

Formula 1 wherein $R_1$ and $R_3$ are H or methyl, $R_2$ and R4 are methyl, said process comprising reacting methyl ethyl ketone with formaldhyde in the presence of ammonia in gas phase conditions in the presence of a catalyst comprising zeolite ZSM-5.

In one embodiment of the invention, $R_1$ is methyl and $R_3$ is H to give 2,3,5-collidine.

In one embodiment of the invention $R_1$ is H and $R_3$ is methyl to give 2,3,6-collidine.

In one embodiment of the invention $R_1$ and $R_3$ are methyl to give 2,3,5,6-tetramethylcollidine.

In one embodiment of the invention, the ZSM-5 catalyst contains at least one element selected from the group consisting of lanthanum, lead, manganese, iron, copper and cobalt.

In one embodiment of the invention A process as claimed in claim 1, wherein the Si/Al ratio in the catalyst is in the range of 15 to 140.

In one embodiment of the invention the amount of said at least one element is between 1 and 10 wt. % of metal to said zeolite.

In one embodiment of the invention said at least one element is contained in the form of an oxide in said zeolite ZSM-5.

In one embodiment of the invention the amount of methyl ethyl ketone is at least one mole per one mole of formaldehyde, and the amount of ammonia is between 0.5 and 5 moles per one mole of the total of methyl ethyl ketone and formaldehyde.

In one embodiment of the invention, wherein methanol is added to the starting materials in an amount of up to 0.5 mole per mole of ethyl methyl ketone.

DETAILED DESCRIPTION OF THE INVENTION

The process of the present invention uses ZSM-5 silica-alumina containing at least one element selected from the group consisting lanthanum, lead; manganese, iron and copper, as a catalyst. At least one element selected from the group consisting of lanthanum, lead, manganese, iron and copper is contained in the catalyst in the form of a metal, an ion and/or a compound. Examples of the compounds of such elements are inorganic compounds such as their oxides, nitrates, hydroxides, carbonates, etc.

The content of alumina in the zeolite varies between 15 and 140 of the silica/alumina ratio. The amount of lanthanum, manganese, iron and copper and/or lead is usually between 1 and 10 wt. %, preferably between 2 and 5 wt. %, based on the weight of the ZSM-5 catalyst. When the content of the alumina and the amount of the element or elements are within the above ranges, respectively, 2,3,5-collidine and 2,3,6-collidine are obtained in good yields, and the deterioration of the catalytic activity of the catalyst with time is suppressed. The presence of water in the formaldehyde decreases the coke formation and increases the lifetime of the catalyst. The catalyst is be prepared from at least one compound selected from the group consisting of inorganic compounds of the above elements (e.g. oxides, halides, sulfates, nitrates, hydroxides, sulfides, silicates, titanates, carbonates, etc.) or organometal compounds of the above elements (e.g. carboxylate salts, organic chelates, etc.) as the source materials for the elements, ZSM-5 catalyst was used as commercial catalyst and it can be prepared by silicon compound (e.g. water glass, silica sol, alkali silicates, etc.) and an aluminium compound (e.g. aluminium nitrate, aluminium sulfate, alumina sol, etc.) in presence of template tripropyl amine by reported literature.

The catalyst of the present invention may be prepared by any conventional method such as impregnation, ion exchange, and the like. For example, ZSM-5 impregnated with the aqueous solution of the above compound(s) of the element(s), dried and calcined. The ZSM-5(30) powder is ion exchanged by treating the powder with the aqueous solution of metal salt solutions of the compound(s) of the element(s) lanthanum, cobalt, lead, copper, manganese and iron and after that it is washed with water, dried and calcined. In the process of the present invention, the catalyst can be used as a fixed bed catalyst or a fluidized bed catalyst.

When the catalyst of the present invention is used as the fixed bed catalyst, it is shaped in the form of a solid tablet with a tabletting machine and then meshed to the 18–30 size. In either case, the shaped catalyst is calcined at a temperature of between 400 and 600° C. for several hours in the atmosphere of air to strengthen the catalyst and to evaporate volatile components off. The calcination of the catalyst after shaping is not always necessary, since the catalyst is heated in a reactor for the gas-phase catalytic reaction.

The process of the present invention can be carried out by any conventional method. For example, a gaseous mixture of methyl ethyl ketone, formaldehyde and ammonia is supplied over the catalyst of the present invention, and catalytically reacted in the gas phase. The amount of methyl ethyl ketone is usually at least one mole, preferably between 0.5 and 2 moles per one mole of formaldehyde. The amount of ammonia is usually between 0.5 and 5 moles, preferably between 1 and 3 moles, per one mole of the total of formaldehyde and methyl ethyl ketone. The reaction temperature for the gas phase catalyst reaction is usually in the range between 300 and 450° C., preferably in the range between 350 and 400° C. The weight hourly space velocity of the mixture of the raw materials is usually between 0.25 and 1 h$^{-1}$. The reaction pressure may be reduced pressure, atmospheric pressure or elevated pressure. Preferably, the reaction pressure is atmospheric pressure.

The possible reaction scheme of the process of the invention is given below:

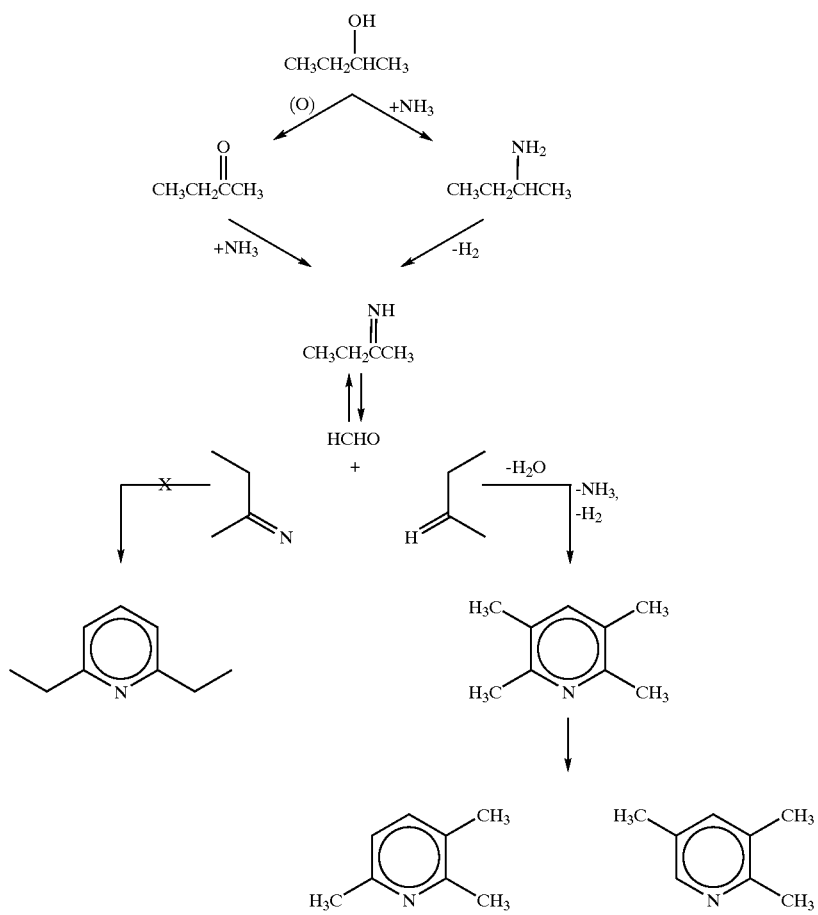

When the process of the present invention is performed in the form of a fixed bed, the catalyst of the present invention is packed in a reactor and heated to a reaction temperature. Then, the mixture of methyl ethyl ketone, formaldehyde and ammonia was allowed to proceed through the gas phase catalytic reaction while maintaining the suitable reaction temperature. Thus, a reaction product containing 2,3,5-collidine, 2,3,6-collidine and 2,3,5,6-tetramethylpyridine is obtained.

The reaction product gas is condensed by cooling, or trapped in a suitable solvent. The condensed or trapped liquid contains 2,3,5-collidine, 2,3,6-collidine and 2,3,5,6-tetramethyl pyridine along with the lutidines and other pyridine derivatives.

EXAMPLES

The present invention will be explained in more detail by the following examples, which do not limit the scope of the invention in any way. Yields in the examples are GC molar yields based on methyl ethyl ketone.

Example 1
Synthesis of Pb Modified ZSM-5:

Four gm of calcined H-ZSM-5 (from Conteka, Swedan) having a Si/Al atomic ratio of 15 was taken in the form of 18–30 mesh and soaked in the 100 ml of solution of lead nitrate containing 0.40 g Pb for several hours then water was dried and catalyst was calcined at 420° C. The lead loading of this catalyst was 4.8% by weight.

Example 2
Synthesis of Co-modified ZSM-5:

The same procedure followed for the preparation of other metal ZSM-5 catalyst by taking their inorganic salts as precursors. Cobalt nitrate in case of Co-ZSM-5.

Example 3

The obtained catalyst was used in the following reaction for the preparation of 2,3,5-collidine and 2-ethyl-5-methylpyridine.

The HZSM-5(15) catalyst (4 g) was packed in a glass tube reactor having an inner diameter of mm with length of 65 mm and the catalyst-packed part of the tube was heated to 400° C. Then, a mixture of methyl ethyl ketone, formaldehyde and ammonia in a molar ratio of 1:1:5 were passed through the catalyst-packed part of the reactor at a weight hourly space velocity of 0.5 hr$^{-1}$. The reaction gas product, which exited from the reactor in the first 4 hour period from the start of the reaction, was condensed by cooling, and the condensate was analyzed by gas chromatography. The yields of 2,3,5-collidine and 2,3,6-collidine were 32.2% and 23.6%, respectively and tetramethyl pyridine is 6.1% along with the other pyridine bases. At the conversion of methyl ethyl ketone was 95.4%. The results are given in Table 1 below:

TABLE 1

| | Wt % |
|---|---|
| Conversion of MEK | 95.4 |
| 2,3,5-collidine | 32.2 |
| 2,3,6-collidine | 23.6 |
| 2,3,5,6-tetramethyl pyridine | 6.1 |
| Lutidines | — |
| Pyridine and picolines | — |

Example 4

2,3,5-Collidine and 2,3,6-collidine were prepared in the same manner as in Example 3 by using the HZSM-5 catalyst with Si:Al ratio of 20.5. The yields of 2,3,5-collidine and 2,3,6-collidine are in the fourth hour from the start of the reaction were 36.6% and 22.0/%, respectively at the conversion of methyl ethyl ketone was 92.0%. The results are given in Table 2 below:

TABLE 2

| | Wt % |
|---|---|
| Conversion of MEK | 92.0 |
| Yield of 2,3,5-collidine | 36.6 |
| Yield of 2,3,6-collidine | 22.0 |
| Yield of 2,3,5,6-tetramethyl pyridine | 7.6 |

Example 5

2,3,5-Collidine and 2,3,6-collidine were prepared in the same manner as in Example 3 by using the HZSM-5 catalyst with Si:Al ratio of 115. The yields of 2,3,5-collidine and 2,3,6-collidine are in the third hour from the start of the reaction were 37.7% and 21.8%, respectively at the conversion of MEK was 95.9%. The results are given in Table 3 below:

TABLE 3

| | Wt % |
|---|---|
| Conversion of MEK | 95.9 |
| Yield of 2,3,5-collidine | 37.7 |
| Yield of 2,3,6-collidine | 21.8 |
| Yield of 2,3,5,6-tetramethyl pyridine | — |

Example 6

2,3,5-Collidine and 2,3,6-collidine were prepared in the same manner as in Example 3 by using the modified HZSM-5 catalyst with Pb (5 wt %). The yields of 2,3,5-collidine and 2,3,6-collidine are in the fourth hour from the start of the reaction were 39.4% and 27.4%, respectively and yield of tetramethyl pyridine is 7.3%, others contain the pyridine bases like lutidine and picolines. Below table gives a typical product distribution over this catalyst. The results are given in Table 4 below:

TABLE 4

| | Wt % |
|---|---|
| Conversion of MEK | 90.8 |
| 2,3,5-collidine | 39.4 |
| 2,3,6-collidine | 27.4 |
| 2,3,5,6-tetramethyl pyridine | 7.6 |
| Lutidines | 4.2 |
| Pyridine and picolines | 12.5 |

Example 7

2,3,5-Collidine and 2,3,6-collidine were prepared in the same manner as in Example 3 by using the modified HZSM-5 catalyst with Fe (5 wt %). The yields of 2,3,5-collidine and 2,3,6-collidine are in the fourth hour from the start of the reaction were 34.5% and 22.2%, respectively and yield of tetramethyl pyridine is 4.6 %, contain the pyridine bases like lutidine and picolines at the conversion of 93.5%. The results are given in Table 5 below:

TABLE 5

| | Wt % |
|---|---|
| Conversion of MEK | 93.5 |
| Yield of 2,3,5-collidine | 34.5 |
| Yield of 2,3,6-collidine | 22.2 |
| Yield of 2,3,5,6-tetramethyl pyridine | 4.6 |

Example 8

2,3,5-Collidine and 2,3,6-collidine were prepared in the same manner as in Example 3 by using the modified HZSM-5 catalyst with La (5wt %). The yields of 2,3,5-collidine and 2,3,6-collidine are in the fourth hour from the start of the reaction were 35.0% and 19.5%, respectively and yield of tetramethyl pyridine is 7.7%, others contain the pyridine bases like lutidine and picolines at the conversion of MEK is 99.3%

Example 9

The reaction was carried out in the same manner as in Example 6 except that the reaction temperature is 380° C. The yield of 2,3,5-collidine and 2,3,6-collidine are 34.3% and 24.0% respectively at the conversion of MEK is 99.0%.

Example 10

2,3,5-Collidine and 2,3,6-collidine were prepared in the same manner as in Example 3 except that the weight hourly space velocity was changed to 0.375. The yields of 2,3,5-collidine and 2,3,6-collidine in the first four hour period from the start of the reaction were 31.2% and 22.3, respectively.

Example 11

Then, 2,3,5-collidine and 2,3,6-collidine were prepared in the same manner as in Example 3 except that the reaction was carried out with 2 butanol in place of methyl ethyl ketone. The yields of 2,3,5-collidine and 2,3,6-collidine in the first four hour period from the start of the reaction were 18.7% and 18.7%, respectively at the conversion of 2-butanol is 77.2%.

ADVANTAGES OF THE INVENTION

The present invention provides a process that comprises of environmentally clean and economical technology, wherein the catalyst can be reused and easily recycled.
The process provides an eco-friendly method with high selectivity towards the product.
This method provides a selective heterogeneous catalyst with longer life which can be recycled and reused several times.
Further, this method provides a route, wherein the kind and composition of collidines and tetramethyl pyridines can be obtained by judiciously varying the carbonyl compounds.
It also provides an efficient and economical method for synthesizing collidines from methyl ethyl ketone and formaldehyde with ammonia over ZSM-5 catalysts.

We claim:

1. A process for synthesizing collidines comprising contacting methyl ethyl ketone or 2-butanol with formaldehyde in the presence of ammonia in gas phase and a zeolite ZSM-5 catalyst under reaction conditions effective to cause formation of a reaction product comprising a compound of formula 1:

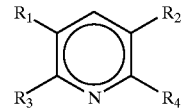

Formula 1 wherein each of $R_1$ and $R_3$ is either H or methyl, and each of $R_2$ and $R_4$ is methyl, said reaction conditions including a temperature in the range of 350–420° C. and a weight hourly space velocity in a range of 0.25 to 1.00 $h^{-1}$.

2. The process as claimed in claim 1, wherein the reaction product comprises 2,3,5-collidine.

3. The process as claimed in claim 1, wherein the reaction product comprises 2,3,6collidine.

4. The process as claimed in claim 1, wherein the reaction product comprises 2,3,5,6-tetramethyl pyridine.

5. The process as claimed in claim 1, wherein the zeolite ZSM 5 catalyst contains at least one element selected from the group consisting of lanthanum, lead, manganese, iron, copper and cobalt.

6. The process as claimed in claim 1, wherein the catalyst comprises an Si/Al ratio in a range of 15 to 140.

7. The process as claimed in claim 5, wherein the at least one element is present in the catalyst in an amount of between 1 and 10 wt %.

8. The process as claimed in claim 5, wherein said at least one element is contained in the form of an oxide in said zeolite ZSM-5 catalyst.

9. The process as claimed in claim 1, wherein reactants comprising the methyl ethyl ketone, formaldehyde, and ammonia are introduced into a reactor containing said catalyst to cause said contacting, the methyl ethyl ketone being present in the reactor in an amount of at least one mole per one mole of formaldehyde, and the ammonia being present in the reactor in an amount of between 0.5 and 5 moles per one mole of the total of the methyl ethyl ketone and formaldehyde.

10. The process as claimed in claim 1, wherein reactants comprising the methyl ethyl ketone, formaldehyde and ammonia are introduced into a reactor containing said catalyst to cause said contacting.

11. The process as claimed in claim 10, wherein methanol is added to the reactor in an amount of up to 0.5 mole per mole of the methyl ethyl ketone.

12. The process as claimed in claim 10, wherein the reactants consist essentially of the methyl ethyl ketone, formaldehyde and ammonia.

13. The process as claimed in claim 1, wherein reactants comprising the 2-butanol, formaldehyde and ammonia are introduced into a reactor containing said catalyst to cause said contacting.

14. The process as claimed in claim 13, wherein the reactants consist essentially of the 2-butanol, formaldehyde and ammonia.

15. The process as claimed in claim 1, wherein the zeolite ZSM-5 catalyst is selected such that the reaction product comprises 2,3,5-collidine and 2,3,6-collidine.

16. The process as claimed in claim 1, wherein the zeolite ZSM-5 catalyst is selected such that the reaction product comprises 2,3,5-collidine, 2,3,6-collidine and 2,3,5,6-tetramethyl pyridine.

* * * * *